United States Patent
Wang et al.

(10) Patent No.: US 6,407,262 B1
(45) Date of Patent: Jun. 18, 2002

(54) PROCESS FOR THE PREPARATION OF RAMIPRIL

(75) Inventors: Zhi-Xian Wang; Cameron McPhail, both of Brantford (CA)

(73) Assignee: Brantford Chemicals Inc., Brantford (CA)

( * ) Notice: Subject to any disclaimer, the term of this patent is extended or adjusted under 35 U.S.C. 154(b) by 0 days.

(21) Appl. No.: 09/990,278

(22) Filed: Nov. 23, 2001

(51) Int. Cl.$^7$ ............................................. C07D 209/52
(52) U.S. Cl. ...................................................... 548/452
(58) Field of Search ........................................ 548/452

(56) References Cited

U.S. PATENT DOCUMENTS

| 4,587,258 A | * | 5/1986 | Gold et al. | .................. | 514/412 |
| 5,977,380 A | | 11/1999 | Yang et al. | .................. | 548/533 |

FOREIGN PATENT DOCUMENTS

| CA | 1338162 | 3/1996 |
| CN | 1106386 | 8/1995 |
| EP | 79022 | 3/1986 |
| EP | 50800 | 6/1986 |
| EP | 115345 | 1/1988 |
| ES | 549251 | 12/1985 |
| ES | 549789 | 12/1985 |
| ES | 2004804 | 2/1989 |

OTHER PUBLICATIONS

V. Teetz, et al., Synthesis of Unnatural Amino Acids: (S,S,S)–2–Azabicyclol[3.3.0]Octane–3–Carboxylic Acid, Tetrahedron Letters, 25(40), 1984, 4479–4482.

L.M. Harwood, et al., Tandem Generation and Intramolecular Trapping of Chiral Stabilised Azomethine Ylids with Alkyne Dipolarophiles, Tetrahedron Letters, 34(41), 1993, 6603–6606.

H. Urbach, et al., Enantioselective Synthesis of 1S,3S,5S–and 1R, 3S,5R–2–Azabicclo[3.3.0]Octane–3–Carboxylic Acid Starting from L–Serine, Heterocycles, 28(2), 957–965, 1989.

J. Martens, et al., Enantiomerentrennung der (1RS,3RS,5RS)–2–Azabicyclo[3.3.0]octan–3–carbonsäure, einem chiralen Baustein für den ACE–Inhibitor Ramipril, Journal f. Prakt. Chemie, 1990, 332(6), 1111–1117.

* cited by examiner

*Primary Examiner*—T. A. Solola
*Assistant Examiner*—Rebecca Anderson
(74) *Attorney, Agent, or Firm*—Marcelo K. Sarkis; Ivor M. Hughes; Neil H. Hughes

(57) ABSTRACT

A process for separating diastereomeric mixtures of compounds of formula 1 and formula 2

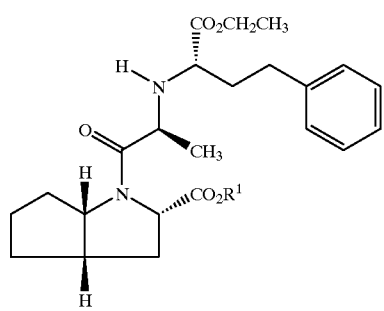

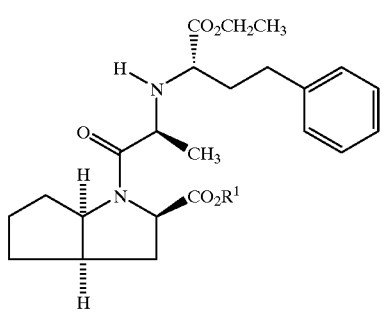

wherein $R^1$=H or $R^1$ denotes a carboxyl-esterifying group selected from $C_1$–$C_6$ alkyl and $C_7$–$C_8$ aralkyl, by treating the mixture of 1 and 2 with a solvent or mixture of solvents to obtain a substantially pure compound of formula 1.

36 Claims, No Drawings

PROCESS FOR THE PREPARATION OF RAMIPRIL

FIELD OF INVENTION

The present invention relates to a process for the production of inhibitors of ACE (Angiotensin Converting Enzyme) and, in particular, to a process for separation of diastereomeric mixtures of compounds of formula 1 and 2.

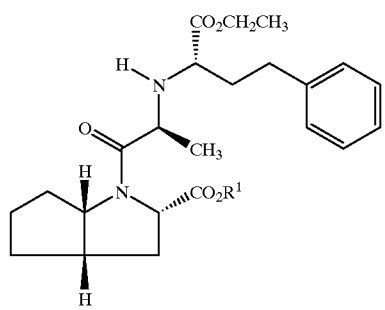

1

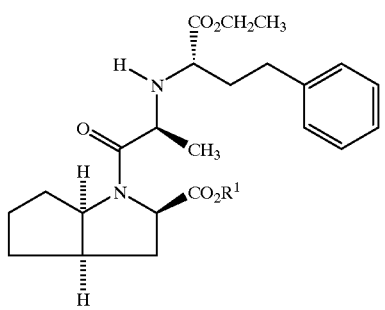

2 wherein $R^1$=H or $R^1$ denotes a carboxyl-esterifying group, such as $C_1$–$C_6$ alkyl, or $C_7$–$C_8$ aralkyl.

BACKGROUND OF THE INVENTION

The previously reported syntheses of Ramipril (1, wherein $R^1$=H) use two approaches. The first approach utilizes the reaction of racemic amino esters 4a and 4b ($R^2$ denotes a carboxyl-esterifying group, such as $C_1$–$C_6$ alkyl, $C_7$–$C_8$ aralkyl, preferably benzyl or tert-butyl)

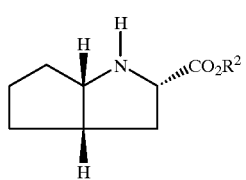

4a

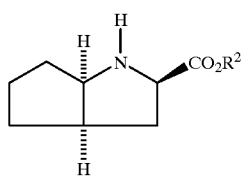

4b with a compound of formula 3, wherein the atoms indicated with an asterisk have the S configuration,

3 using amide formation methods known in peptide chemistry (such as those described in CA 1,338,162, EP 79022, U.S. Pat. No. 5,977,380, ES 549789 and ES 2004804, for example) to prepare the mixture of compounds 5 and 6,

5

6 wherein $R^2$ denotes a carboxyl-esterifying group, such as $C_1$–$C_6$ alkyl, or $C_7$–$C_8$ aralkyl. This route gives a 1:1 mixture of diastereomers 5 and 6 from which the desired diastereomer 5 is separated using silica gel chromatography. Subsequent removal of the protecting group by hydrogenolysis or treatment with an acid or base yields Ramipril (compound of formula 1, $R^1$=H). This approach is disclosed in EP 79022, for example. This procedure suffers from the disadvantage of requiring two additional synthetic steps to install the carboxyl protecting group of 4a and 4b and to remove the ester group on 5, and the disadvantage of requiring costly and hard-to-implement silica gel chromatographic purification to separate 5 and 6.

The compound of the formula 3 is well known (for example in European patent 037, 231) and is accessible in various ways. Several routes for the synthesis of the racemic mixture 4a and 4b have been disclosed in the patent literature (Patent EP 79022, Patent EP 50800, Patent ES 549251, Patent CN 1106386 for example) and in the literature (V. Teetz et al *Tetrahedron Letters*, 1984, 25(40), 4479–4482, for example).

The second approach utilizes enantiopure amino ester 4a ($R^2$ denotes a carboxyl-esterifying group, such as $C_1$–$C_6$ alkyl, $C_7$–$C_8$ aralkyl, preferably benzyl or tert-butyl) as one partner in a coupling reaction with compound 3, using the methods commonly known in peptide chemistry (such as those described in CA 1,338,162, EP 79022, U.S. Pat. No. 5,977,380, ES 549789 and ES 2004804, for example) to prepare 5 wherein $R^2$ denotes a carboxyl-esterifying group, such as $C_1$–$C_6$ alkyl or $C_7$–$C_8$ aralkyl.

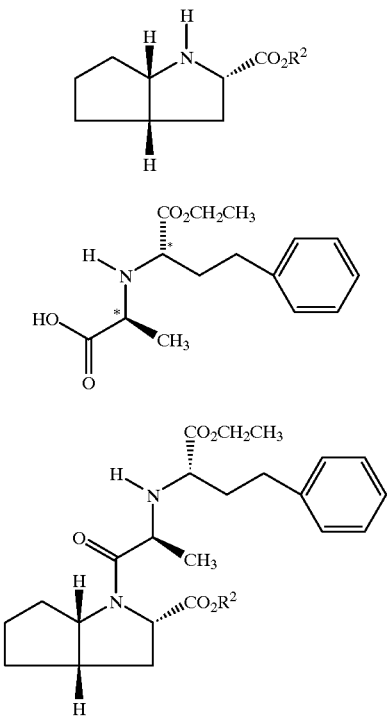

When the compound of formula 5 (wherein $R^2$ denotes a carboxyl-esterifying group, such as $C_1$–$C_6$ alkyl or $C_7$–$C_8$ aralkyl) is prepared using a coupling of 4a with 3, the ester protecting group ($R^2$) is removed by hydrogenolysis or treatment with an acid or base, then the resulting product (1, Ramipril where $R^1$=H) is crystallized from a substantially pure solution. However, this general route also has its difficulties. Firstly, the efficient large-scale enantioselective synthesis of chirally pure 4a has not been reported. However, there are two reported enantioselective syntheses of compound 4a or derivatives. An enantioselective synthesis of 7a was reported by L. M. Harwood and L. C. Kitchen (*Tetrahedron Letters*, 1993, 34(41), 6603–6606) but the chemistry does not appear suitable to scale-up and the overall yield is low (13%)

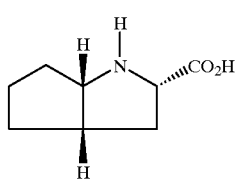

An enantioselective (but not diastereoselective) route, reported by H. Urbach and R. Henning, (Heterocycles, 1989, 28(2), 957–965) gave 4a ($R^2$=Benzyl) in an overall yield of 5.5%, which appears to be too low for commercial implementation.

There are three reported methods for the resolution of bicyclic amino acids of this type. An enantioenriched sample of amino acid 7a was obtained by resolution of 7a and 7b is reported in patent ES 549251. Amino acid 7a can be converted to amino ester 4a by methods known to those skilled in the art.

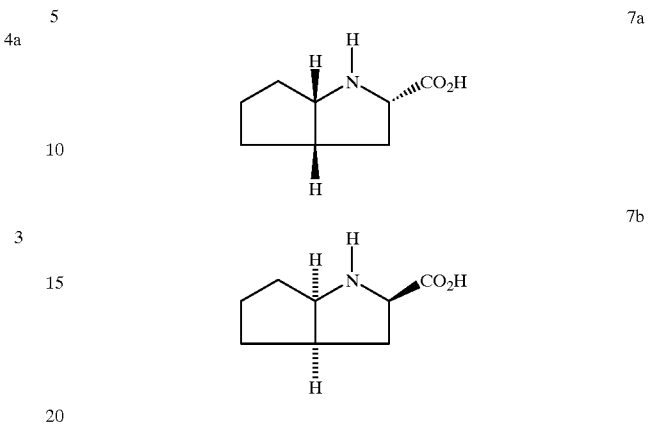

This resolution removes 7b from a mixture of 7a and 7b, giving, after removal of the chiral base by acidification of the residue, a 52% yield of material (7a) in unspecified optical purity. However, this resolution uses an expensive chiral amine (S)-1-(1-naphthyl)ethylamine.

The other reported resolution methods resolve the racemic mixture of 4a and 4b. A resolution separating 4a ($R^2$= carboxyl esterifying group) from a racemic mixture of 4a and 4b using N-acyl derivatives of optically active R or S amino acids containing a phenyl nucleus has been disclosed in patent EP 115345. This procedure gives 4a (wherein $R^1$=Benzyl) in a yield corresponding to 102.1% of theoretical, with an optical purity of 87%. This resolution, as disclosed, uses the toxic solvent dichloromethane and an expensive anti-solvent cyclohexane.

A resolution protocol for the obtention of 4a from a racemic mixture of 4a and 4b has been reported using S-mandelic acid (J. Martens and S. Lubben, *Journal für Prakt. Chemie* 1990, 332(6), 1111–1117). This protocol returns 4a in high purity (>98%) but in lower yield (43% for the mandelic acid salt). Unfortunately, these two approaches require a sequence of steps when used in the production of Ramipril, as it is reported: protection of the amino acid as a carboxylic ester, free-basing the HCl salt, formation of the salt with the resolving agent, isolation of the diastereomeric salt, free-basing the diastereomeric salt, and formation of the HCl salt. Using this many steps to produce the material consumes expensive plant time and reduces efficiency.

SUMMARY OF THE INVENTION

According to a first aspect of the present invention there is provided a process for separating diastereomeric mixtures of (2S,3aS,6aS)-1-[(S)-2-[[(S)-1-(ethoxycarbonyl)-3-phenylpropyl]amino]propanoyl]octahydro-cyclopenta[b] pyrrole-2-carboxylic acid derivative of compound formula 1 and (2R,3aR,6aR)-1-[(S)-2-[[(S)-1-(ethoxycarbonyl)-3-phenylpropyl]amino]propanoyl]octahydrocyclopenta[b] pyrrole-2-carboxylic acid derivative of compound of formula 2, the process comprising:

(a) treating the mixture of 1 and 2 with a solvent or a mixture of solvents selected from a group consisting of $C_2$–$C_4$ nitrile solvents, $C_1$–$C_6$ alcohol solvents, $C_6$–$C_8$ aromatic hydrocarbon solvents, $C_3$–$C_{10}$ ether solvents, $C_3$–$C_6$ ketone solvents, $C_2$–$C_7$ ester solvents, $C_1$ to $C_3$ chlorinated solvents, and $C_5$–$C_{10}$ hydrocarbon solvents, (b) adding an organic or inorganic acid, if desired, selected from a group consisting of benzoic acid, mandelic acid, maleic acid, fumaric acid, methane sulfonic acid, toluene sulfonic acid, hydrochloric acid, hydrobromic acid, sulfuric acid, and phosphoric acid, (c) allowing the compound of formula 1 to precipitate and filtering the slurry to obtain a solid compound of formula 1, where $R^1$=H or $R^1$ denotes a carboxyl-esterifying group, such as $C_1$–$C_6$ alkyl, preferably tert-butyl, and $C_7$–$C_8$ aralkyl, preferably benzyl.

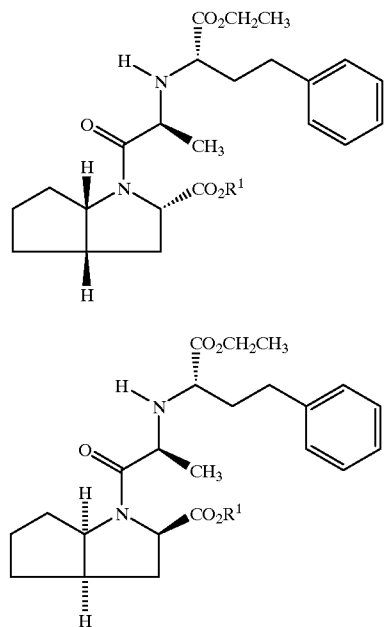

The process involves the treatment of an equal or unequal amount of diastereomeric compounds 1 and 2 with a solvent or a mixture of solvents, treating the mixture of 1 and 2 in a solvent with an inorganic or organic acid, if necessary, stirring the mixture of 1 and 2 in a solvent or a mixture of solvents, allowing the desired isomer to precipitate with or without seeding, adding a solvent (or a mixture of solvents) if desired, and isolating the desired substantially pure compound 1 at a temperature of −50 to 50° C. as a solid. The isolated product 1 may be treated with an acid or base if necessary, or subjected to hydrogenolysis if necessary to give Ramipril.

When $R^1$ is benzyl, for example, the preferred acid salt is maleic acid and the salt produced is (2S,3aS,6aS)-1-[(S)-2-[[(S)-1-(ethoxycarbonyl)-3-phenylpropyl]-amino]propanoyl]octahydrocyclopenta[b]pyrrole-2-carboxylic acid benzyl ester maleic acid salt. This salt is new and is a useful intermediate for manufacturing the compound Ramipril.

According to a second aspect of the present invention there is provided a process for separation of a mixture of (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivatives of the formula 1 and (2R,3aR,6aR)-1-[(S)-2-[[(S)-1-(ethoxycarbonyl)-3-phenylpropyl]amino]propanoyl]octahydrocyclopenta[b]pyrrole-2-carboxylic acid derivative of formula 2, wherein $R^1$=H, the process comprising:

(a) treating the mixture of 1 and 2 with a solvent or mixture of solvents selected from a group consisting of $C_2$–$C_4$ nitrile solvents, $C_1$–$C_6$ alcohol solvents, $C_6$–$C_8$ aromatic hydrocarbon solvents, $C_3$–$C_{10}$ ether solvents, $C_3$–$C_6$ ketone solvents, $C_2$–$C_7$ ester solvents, $C_1$–$C_3$ halogenated solvents, and $C_5$–$C_{10}$ hydrocarbon solvents, (b) adding an organic or inorganic base selected from a group consisting of sodium hydroxide, lithium hydroxide, potassium hydroxide, sodium bicarbonate, sodium carbonate, potassium carbonate, tert-butylamine, triethylamine, piperidine, aniline, n-butylamine or dicyclohexylamine, then filtering the slurry to obtain a solid salt of compound of formula 1.

Suitable solvents or solvent mixtures of the present invention include but are not limited to $C_2$–$C_4$ nitrile solvents such as acetonitrile, propionitrile and the like, $C_1$–$C_6$ alcohols such as ethanol, methanol and the like, $C_6$–$C_9$ aromatic hydrocarbons such as benzene, toluene, xylenes and the like, $C_3$–$C_{10}$ ethers such as dimethoxyethane, diethyl ether, tetrahydrofuran, diisopropyl ether and the like, $C_3$–$C_6$ ketone solvents such as methyl isobutyl ketone, methyl isopropyl ketone and the like, $C_2$–$C_7$ ester solvents such as ethyl acetate, ethyl propionate, isopropyl acetate and the like, $C_5$–$C_{10}$ hydrocarbons such as hexanes, heptanes, octanes, and the like; and $C_1$ to $C_3$ chlorinated solvents such as dichloromethane, chloroform and the like. Suitable organic acids for this process include but are not limited to $C_1$–$C_8$ acids and diacids such as benzoic acid, mandelic acid, maleic acid, fumaric acid, and the like. Suitable inorganic acids for this process include but are not limited to hydrochloric acid, hydrobromic acid, sulfuric acid, phosphoric acid, and the like. Suitable inorganic and organic bases for this process include but are not limited to sodium hydroxide, lithium hydroxide, potassium hydroxide, sodium bicarbonate, sodium carbonate, potassium carbonate, tert-butylamine, triethylamine, piperidine, aniline, n-butylamine or dicyclohexylamine, and the like.

The preferred organic acid, when required, is maleic acid, especially when $R^1$ is a carboxyl esterifying group and preferably when $R^1$ is benzyl. The preferred solvents are, for instance, ethyl acetate or a mixture containing ethyl acetate, acetonitrile, butyl acetate, and isopropyl acetate, which may be present in a mixture with, for instance, diisopropyl ether and/or ethanol and/or acetonitrile. The preferred precipitation temperature range is −15 to 30° C. and the ratio of the diastereomeric mixture is preferably between 8:1 to 1:5 for compound of formula 1 and 2 respectively.

DETAILS OF THE INVENTION

In the present invention, a (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivative of formula 1 is separated from an equal or unequal amount of (2R,3aR, 6aR)-1 -[(S)-2-[[(S)-1-(ethoxycarbonyl)-3-phenylpropyl]amino]propanoyl]-octahydrocyclopenta[b]pyrrole-2-carboxylic acid derivative of formula 2, wherein $R^1$=H or $R^1$ denotes a carboxyl-esterifying group, such as ($C_1$–$C_6$) alkyl, ($C_7$–$C_8$) aralkyl by treatment with a solvent (or a mixture of solvents) at a temperature between −50 and 50° C., treating the mixture with an organic or inorganic acid if necessary or an inorganic or organic base if necessary, stirring the mixture in a solvent or a mixture of solvents at −50 to 50° C., allowing compound of formula 1 to precipitate at −50 to 50° C. with or without seeding, adding a solvent or a mixture of solvents, if desired, to give substantially pure compound of formula 1, at a temperature between −50 and 50° C., as a solid. Scheme 1 depicts this process.

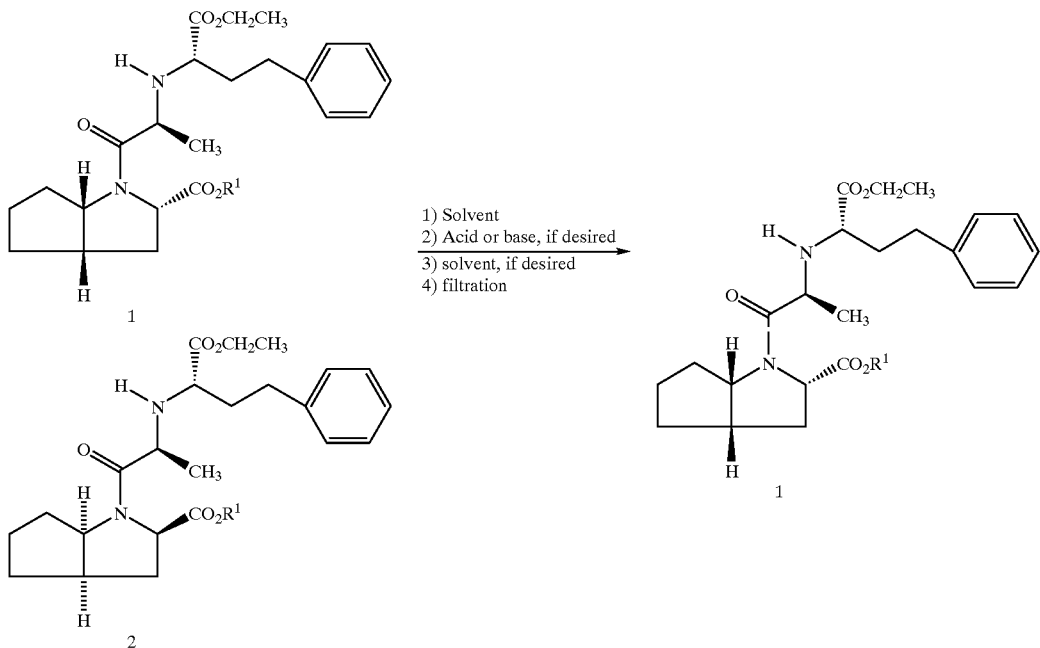

The isolated compound of formula 1, where $R^1$ is defined as above, may be treated with an acid or base if necessary, or subjected to hydrogenolysis if necessary, to give Ramipril (1, where $R^1$=H).

Suitable solvents or solvent mixtures for this separation include but are not limited to $C_2$–$C_4$ nitrile solvents such as acetonitrile, propionitrile and the like; $C_1$–$C_6$ alcohols such as ethanol, methanol and the like; $C_6$–$C_9$ aromatic hydrocarbons such as benzene, toluene, xylenes and the like; $C_3$–$C_{10}$ ethers such as dimethoxyethane, diethyl ether, tetrahydrofuran, diisopropyl ether and the like; $C_3$–$C_6$ ketone solvents such as methyl isobutyl ketone, methyl isopropyl ketone and the like; $C_2$–$C_7$ ester solvents such as ethyl acetate, ethyl propionate, isopropyl acetate and the like; $C_5$–$C_{10}$ hydrocarbons such as hexanes, heptanes, octanes, and the like; $C_1$ to $C_3$ chlorinated solvents such as dichloromethane, and the like. Suitable organic acids for this process include but are not limited to $C_1$–$C_8$ acids and diacids such as benzoic acid, mandelic acid, maleic acid, fumaric acid, and the like. Suitable inorganic acids for this process include but are not limited to hydrochloric acid, hydrobromic acid, sulfuric acid, phosphoric acid, and the like. Suitable inorganic and organic bases for this process include but are not limited to sodium hydroxide, lithium hydroxide, potassium hydroxide, sodium bicarbonate, sodium carbonate, potassium carbonate, tert-butylamine, triethylamine, piperidine, aniline, n-butylamine or dicyclohexylamine, and the like.

The preferred carboxyl esterifying group for this process is $R^1$=benzyl. The preferred acid salt, when required, is maleic acid. The preferred solvents are, for instance, toluene, dimethoxyethane, ethyl acetate, isopropyl acetate, which may or be present in a mixture with, for instance, diisopropyl ether and/or ethanol and/or acetonitrile. The precipitation temperature can range between −50 and 50° C. and the preferred temperature range is −15 to 30° C.

The following non-limiting examples show the process for separating 1 from 2 ($R^1$ defined as above), via the processes of the present invention.

EXAMPLE 1

Separation of (2S,3aS,6aS)-1-[(S)-2-[[(S)-1-(ethoxycarbonyl)-3-phenylpropyl]-amino]propanoyl]octahydrocyclopenta[b]pyrrole-2-carboxylic acid from an approximately equimolar amount of (2R,3aR,6aR)-1-[(S)-2-[[(S)-1-(ethoxycarbonyl)-3-phenylpropyl]amino]propanoyl]octahydrocyclopenta[b]pyrrole-2-carboxylic acid using ethyl acetate/diisopropyl ether solvent.

A reaction solution of an approximately equimolar mixture of 1 ($R^1$=H) and 2 ($R^1$=H) (theoretical yield of 1+2= 3.68 g) was prepared in ethanol solution using methods described in the prior art. This mixture was evaporated on the rotary evaporator at a bath temperature of 40° C. to give a light yellow syrup. This syrup was dissolved in 10 mL of ethyl acetate. The resulting solution was seeded with 10 mg of ramipril seed crystals, and the resulting light suspension was stirred at a bath temperature of 19° C. Over the next two hours, 11 mL of diisopropyl ether was added to the reaction, in small portions. The reaction mixture was then filtered and washed with three 5-mL portions of 1:1 ethyl acetate/diisopropyl ether. The solids were dried under vacuum overnight at 40–45° C., to give 1.13 g (30.6% yield, 61.2% of theoretical recovery) of Ramipril (1, $R^1$=H). The proton NMR spectrum indicated that no 2 ($R^1$=H) was present.

EXAMPLE 2

Separation of (2S,3aS,6aS)-1-[(S)-2-[[(S)-1-(ethoxycarbonyl)-3-phenylpropyl]-amino]propanoyl]octahydrocyclopenta[b]pyrrole-2-carboxylic acid from an approximately equimolar amount of (2R,3aR,6aR)-1-[(S)-2-[[(S)-1-(ethoxycarbonyl)-3-phenylpropyl]amino]propanoyl]octahydrocyclopenta[b]pyrrole-2-carboxylic acid using isopropyl acetate solvent.

A reaction solution of an approximately equimolar mixture of 1 ($R^1$=H) and 2 ($R^1$=H) (theoretical yield of 1+2= 2.29 g) was prepared in ethanol/acetonitrile solution using methods described in the prior art. This mixture was evaporated on the rotary evaporator to a mass of 4.45 g. A 25-mL portion of isopropyl acetate was added to the mixture, and the mixture was evaporated to a mass of 5.1 g, using the rotary evaporator. A 25-mL portion of isopropyl acetate was added to the mixture, which was then evaporated to a mass of 5.65 g on the rotary evaporator. A 3.41 g portion of isopropyl acetate was added to the mixture. The resulting solution was stirred at 20–25° C., and the reaction was seeded with approximately 5 mg of Ramipril. After stirring and allowing solids to precipitate for 6 hours, the mixture was filtered and washed with three 0.5-mL portions of isopropyl acetate. After drying overnight at 40–45° C., 0.53 g (45.8% of theoretical, 23% yield) of Ramipril (1, $R^1$=H) was obtained. The proton NMR spectrum showed none of isomer 2 ($R^1$=H) was present, and the chromatographic purity of the sample exceeded 99.0%.

EXAMPLE 3

Separation of (2S,3aS,6aS)-1-[(S)-2-[[(S)-1-(ethoxycarbonyl)-3-phenylpropyl]-amino]propanoyl] octahydrocyclopenta[b]pyrrole-2-carboxylic acid from an approximately equimolar amount of (2R,3aR,6aR)-1-[(S)-2-[[(S)- 1-(ethoxycarbonyl)-3-phenylpropyl]amino] propanoyl]octahydrocyclopenta[b]pyrrole-2-carboxylic acid using butyl acetate solvent.

Substituting the isopropyl acetate in EXAMPLE 2 with butyl acetate resulted in a 0.49 g (42% of theoretical, 21% yield) of Ramipril (1, $R^1$=H). The proton NMR spectrum showed none of the undesired isomer (2, $R^1$=H) was present, and the chromatographic purity of the sample exceeded 99.0%.

EXAMPLE 4

Separation of (2S,3aS,6aS)-1-[(S)-2-[[(S)-1-(ethoxycarbonyl)-3-phenylpropyl]-amino]propanoyl] octahydrocyclopenta[b]pyrrole-2-carboxylic acid from an approximately equimolar amount of (2R,3aR,6aR)-1-[(S)-2-[[(S)-1-(ethoxycarbonyl)-3-phenylpropyl]amino] propanoyl]octahydrocyclopenta[b]pyrrole-2-carboxylic acid using ethyl propionate solvent.

Substituting the isopropyl acetate in EXAMPLE 2 with butyl acetate resulted in a 0.51 g (44% of theoretical, 22% yield) of Ramipril (1, $R^1$=H). The proton NMR spectrum showed that none of the undesired isomer (2, $R^1$=H) was present, and the chromatographic purity of the sample exceeded 99.0%.

EXAMPLE 5

Separation of (2S,3aS,6aS)-1-[(S)-2-[[(S)-1-(ethoxycarbonyl)-3-phenylpropyl]-amino]propanoyl] octahydrocyclopenta[b]pyrrole-2-carboxylic acid benzyl ester maleic acid salt 1 ($R^1$=benzyl) from an approximately equimolar amount of (2R, 3aR,6aR)-1-[(S)-2-[[(S)-1-(ethoxycarbonyl)-3-phenylpropyl]amino]propanoyl]-octahydrocyclopenta[b]pyrrole-2-carboxylic acid benzyl ester maleic acid salt 2 ($R^1$=benzyl) using butyl acetate/ diethyl ether solvent.

A solution of an equimolar mixture of 1 ($R^1$=Benzyl) and 2 ($R^1$=Benzyl) (theoretical yield of 1+2=4.50 g, 9.14 mmol) in ethyl acetate solution ($V_{tot}$=35 mL), was prepared using methods described in the prior art, particularly EP 79022 and ES 2004804. To this solution was added 1.16 g (9.76 mmol) of maleic acid. This slightly cloudy organic solution was evaporated to approximately 5 mL, and was filtered to remove solid particles. The filtrate was evaporated to give a light yellow syrup. A 10-mL portion of butyl acetate was added to the syrup, giving a clear yellow solution. The solution was cooled to −10° C., and 10 mL of diethyl ether was added slowly. The mixture was seeded with 10 mg of (2S,3aS,6aS)-1-[(S)-2-[[(S)-1-(ethoxycarbonyl)-3-phenylpropyl]amino]propanoyl]octahydrocyclopenta[b] pyrrole-2-carboxylic acid benzyl ester maleic acid salt 1 ($R^1$=Benzyl). The mixture was stirred at −10 to −5° C. for 1 hour. The mixture was placed in the refrigerator at −15° C. overnight. After removal from the refrigerator at −15° C. and stirring at −15° C. for 0.5 hours, the mixture was filtered, and the solids washed with ethyl ether/ethyl acetate (1:1). After drying at 40–45° C. in a vacuum oven, 1.52 g (27.6% yield, 55.2% of theoretical) of ramipril benzyl ester maleic acid salt (1, $R^1$=Benzyl) was obtained as a white solid. The proton NMR spectrum indicated that no undesired isomer (2, $R^1$=Benzyl) was present.

EXAMPLE 6

Separation of (2S,3aS,6aS)-1-[(S)-2-[[(S)-1-(ethoxycarbonyl)-3-phenylpropyl]-amino]propanoyl] octahydrocyclopenta[b]pyrrole-2-carboxylic acid benzyl ester maleic acid salt 1 ($R^1$=Benzyl) from an approximately equimolar amount of (2R, 3aR,6aR)-1-[(S)-2-[[(S)-1-(ethoxycarbonyl)-3-phenylpropyl]amino]propanoyl]-octahydrocyclopenta[b]pyrrole-2-carboxylic acid benzyl ester maleic acid salt 2 ($R^1$=Benzyl).

A reaction solution of an equimolar mixture of 1 (R=Benzyl) and 2 (R=Benzyl) (theoretical yield of 1+2=4.50 g) in ethyl acetate solution ($V_{tot}$=35 mL), was prepared using methods described in the prior art, particularly EP 79022 and ES 2004804. This solution was evaporated to an oil at a bath temperature of 40–45° C. To this oil was added 1.2 g of maleic acid dissolved in 15 mL of hot ethyl acetate. The mixture was cooled to −10° C. and was seeded with 0.1 g of (2S,3aS,6aS)-1-[(S)-2-[[(S)-1-(ethoxycarbonyl)-3-phenylpropyl]amino]propanoyl]octahydro-cyclopenta[b] pyrrole-2-carboxylic acid benzyl ester maleic acid salt 1. After 2.5 hours at −5 to −10° C., the solid was filtered and washed with ether/ethyl acetate and dried to give 1.4 g (23.6% yield, 47.2% recovery) of ramipril benzyl ester maleic acid salt (1, R=Bn), as a white solid. The proton NMR spectrum indicated that none of the undesired isomer (2) was present.

EXAMPLE 7

Preparation of Ramipril from (2S,3aS,6aS)-1-[(S)-2-[[(S)-1-(ethoxycarbonyl)-3-phenylpropyl]amino]propanoyl] octahydrocyclopenta[b]pyrrole-2-carboxylic acid benzyl ester maleic acid salt 1 ($R^1$=Benzyl).

A 1.0 g portion of (2S,3aS,6aS)-1-[(S)-2-[[(S)-1-(ethoxycarbonyl)-3-phenylpropyl]amino]propanoyl] octahydrocyclopenta[b]pyrrole-2-carboxylic acid benzyl ester maleic acid salt 1 was placed into 100 mL of dichloromethane, and was cooled to 0–5° C. Triethylamine (0.19 g) was added to the mixture. The resulting mixture was washed with water, and the organic phase was evaporated to give an oil. This oil was deprotected using hydrogenolysis, as per examples stated in EP 079022 to give Ramipril as a white solid.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for separation of diastereomeric mixtures of (2S,3aS,6aS)-1-[(S)-2-[[(S)-1-(ethoxycarbonyl)-3-phenylpropyl]amino]propanoyl]octahydrocyclopenta-[b]pyrrole-2-carboxylic acid derivatives of the formula 1 and

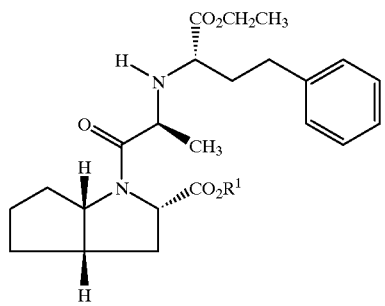

(2R,3aR,6aR)-1-[(S)-2-[[(S)-1-(ethoxycarbonyl)-3-phenylpropyl]amino]propanoyl]-octahydrocyclopenta[b]pyrrole-2-carboxylic acid derivative of formula 2

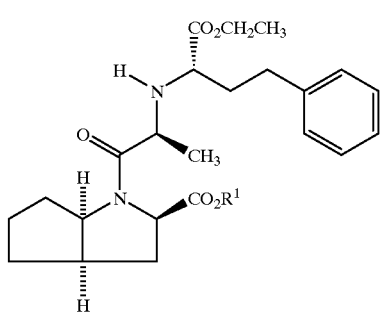

wherein $R^1$=H or $R^1$ denotes a carboxyl-esterifying group selected from $C_1$–$C_6$ alkyl or $C_7$–$C_8$ aralkyl, the process comprising:

(a) treating the midxture of 1 and 2 with a solvent or a mixture of solvents selected from a group consisting of $C_2$–$C_4$ nitrile solvents, $C_1$–$C_6$ alcohol solvents, $C_6$–$C_8$ aromatic hydrocarbon solvents, $C_3$–$C_{10}$ ether solvents, $C_3$–$C_6$ ketone solvents, $C_2$–$C_7$ ester solvents, $C_1$ to $C_3$ chlorinated solvents, and $C_5$–$C_{10}$ hydrocarbon solvents, (b) optionally adding an organic or inorganic acid, selected from a group consisting of benzoic acid, mandelic acid, maleic acid, fumaric acid, methane sulfonic acid, toluene sulfonic acid, hydrochloric acid, hydrobromic acid, sulfuric acid, and phosphoric acid, (c) allowing the compound of formula 1 to precipitate and filtering the slurry to obtain a solid compound of formula 1.

2. The process of claim 1 where the (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivative (1) produced is (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid (Ramipril).

3. The process of claim 1 or 2 where the ratio of (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivative (1) to (2R,3aR,6aR)-1-[(S)-2-[[(S)-1-(ethoxycarbonyl)-3-phenylpropyl]amino]propanoyl]octahydrocyclopenta[b]pyrrole-2-carboxylic acid derivative (2) is between 8:1 to 1:5.

4. The process of claim 1 or 2 where the solvent or mixture of solvents are selected from the group consisting of ethyl acetate, butyl acetate, ethyl propionate, isopropyl acetate, tert-butyl methyl ether, diisopropyl ether, toluene, dimethoxyethane, acetonitrile, ethanol and mixtures thereof.

5. The process of claim 1 or 2 where the solvent is ethyl acetate or a mixture containing ethyl acetate.

6. The process of claim 1 or 2 where the solvent is isopropyl acetate or a mixture containing isopropyl acetate.

7. The process of claim 1 or 2 where the solvent is acetonitrile or a mixture containing acetonitrile.

8. The process of claim 1 or 2 where the solvent is butyl acetate or a mixture containing butyl acetate.

9. A process for separating a mixture of (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivatives of the formula 1 and

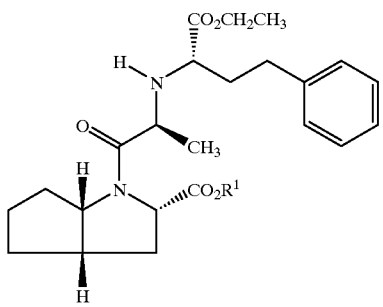

(2R,3aR,6aR)-1-[(S)-2-[[(S)-1-(ethoxycarbonyl)-3-phenylpropyl]amino]propanoyl]-octahydrocyclopenta[b]pyrrole-2-carboxylic acid derivative of formula 2

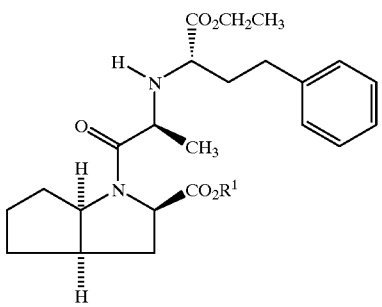

wherein $R^1$ denotes a carboxyl-esterifying group, selected from ($C_1$–$C_6$) alkyl and ($C_7$–$C_8$) aralkyl, the process comprising:

(a) adding a solvent or a mixture of solvents selected from $C_2$–$C_4$ nitrile solvents, $C_1$–$C_6$ alcohol solvents, $C_6$–$C_8$ aromatic hydrocarbon solvents, $C_3$–$C_{10}$ ether solvents, $C_3$–$C_6$ ketone solvents, $C_2$–$C_7$ ester solvents, and $C_5$–$C_{10}$ hydrocarbon solvents, (b) adding an organic or inorganic acid selected from a group consisting of benzoic acid, mandelic acid, maleic acid, fumaric acid, methane sulfonic acid, toluene sulfonic acid, hydrochloric acid, hydrobromic acid, sulfuric acid, and phosphoric acid, (c) allowing the compound of formula 1 to precipitate and filtering the slurry to obtain a solid salt of compound of formula 1.

10. The process of claim 9 wherein $R^1$ is benzyl and the salt produced is the acid addition salt of (2S,3aS,6aS)-1-[(S)-2-[[(S)-1-(ethoxycarbonyl)-3-phenylpropyl]-amino]propanoyl]octahydrocyclopenta[b]pyrrole-2-carboxylic acid benzyl ester.

11. The process of claim 9 or 10 wherein the salt produced is further converted to a free-base by treating with a base and subjected to hydrogenolysis to give (2S,3aS, 6aS)-1-[(S)-2-[[(S)-1-(ethoxycarbonyl)-3-phenylpropyl]amino]propanoyl]-octahydrocyclopenta[b]pyrrole-2-carboxylic acid (Ramipril).

12. The process of claim 9 wherein $R^1$ is tert-butyl and the salt produced is the acid addition salt of (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid tert-butyl ester.

13. The process of claim 9 or 12 wherein the salt produced is further treated with an acid and converted to a free-base by treating with a base to give (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid (Ramipril).

14. The process of claim 9, 10 or 12 where the ratio of (2S,3aS,6aS)-1-[(S)-2-[[(S)-1-(ethoxycarbonyl)-3-phenylpropyl]amino]propanoyl]octahydrocyclopenta[b]-pyrrole-2-carboxylic acid derivative (1) to (2R,3aR,6aR)-1-[(S)-2-[[(S)-1-(ethoxycarbonyl)-3-phenylpropyl]amino]propanoyl]octahydrocyclopenta[b]pyrrole-2-carboxylic acid derivative (2) is between 8:1 to 1:5.

15. The process of claim 11 wherein the salt is maleic acid addition salt.

16. The process of claim 9, 10 or 12 where the solvent or mixture of solvents is selected from the group consisting of ethyl acetate, isopropyl acetate, tert-butyl methyl ether, diisopropyl ether, toluene, dimethoxyethane, acetonitrile, ethanol, butyl acetate, diethyl ether and mixtures thereof.

17. The process of claim 9, 10 or 12 where the solvent is butyl acetate, or a solvent mixture containing butyl acetate.

18. The process of claim 9, 10 or 12 where the solvent is ethyl acetate or a solvent mixture containing ethyl acetate.

19. The process of claim 9, 10 or 12 where the solvent is isopropyl acetate or a solvent mixture containing isopropyl acetate.

20. A process for separation of a mixture of (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivatives of the formula 1 and

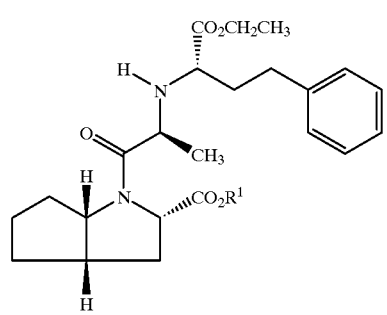

(2R,3aR,6aR)-1-[(S)-2-[[(S)-1-(ethoxycarbonyl)-3-phenylpropyl]amino]propanoyl]-octahydrocyclopenta[b]pyrrole-2-carboxylic acid derivative of formula 2

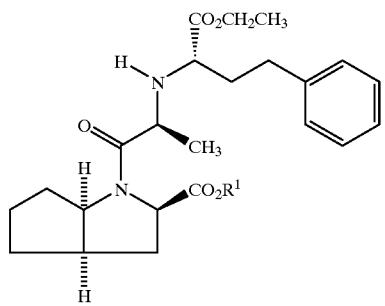

wherein $R^1$=H, the process comprising treating the mixture of 1 and 2 with a solvent or mixture of solvents selected from a group consisting of $C_2$–$C_4$ nitrile solvents, $C_1$–$C_6$ alcohol solvents, $C_6$–$C_8$ aromatic hydrocarbon solvents, $C_3$–$C_{10}$ ether solvents, $C_3$–$C_6$ ketone solvents, $C_2$–$C_7$ ester solvents, $C_1$–$C_3$ halogenated solvents, and $C_5$–$C_{10}$ hydrocarbon solvents, allowing compound of formula 1 to precipitate then filtering the slurry to obtain a solid salt of compound of formula 1.

21. The process of claim 20 where the (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivative (1) produced is (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid (Ramipril).

22. The process of claim 20 or 21 where the ratio of (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivative 1 to (2R,3aR,6aR)-1-[(S)-2-[[(S)-1-(ethoxycarbonyl)-3-phenylpropyl]amino]propanoyl]octahydrocyclopenta[b]pyrrole-2-carboxylic acid derivative 2 is between 8:1 to 1:5.

23. The process of claims 20 or 21 where the solvent or mixture of solvents is selected from the group consisting of ethyl acetate, butyl acetate, ethyl propionate, isopropyl acetate, tert-butyl methyl ether, diisopropyl ether, toluene, dimethoxyethane, acetonitrile, ethanol and mixtures thereof.

24. The process of claims 20 or 21 where the solvent is ethyl acetate or a mixture containing ethyl acetate.

25. The process of claims 20 or 21 where the solvent is isopropyl acetate or a mixture containing isopropyl acetate.

26. The process of claims 20 or 21 where the solvent is acetonitrile or a midxture containing acetonitrile.

27. The process of claims 20 or 21 where the solvent is butyl acetate or a mixture containing butyl acetate.

28. (2S,3aS,6aS)-1-[(S)-2-[[(S)-1-(ethoxycarbonyl)-3-phenylpropyl]amino]-propanoyl]octahydrocyclopenta[b]pyrrole-2-carboxylic acid benzyl ester maleic acid salt.

29. A process for separation of a mixture of (2S,3aS,6aS)-1-[(S)-2-[[(S)-1-(ethoxycarbonyl)-3-phenylpropyl]amino]propanoyl]octahydrocyclopenta[b]pyrrole-2-carboxylic acid derivatives of the formula 1 and

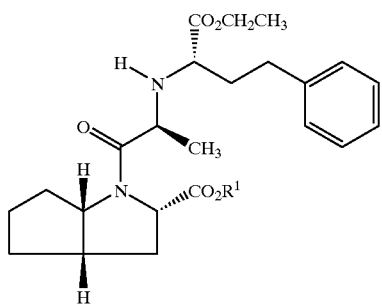

(2R,3aR,6aR)-1-[(S)-2-[[(S)-1-(ethoxycarbonyl)-3-phenylpropyl]amino]propanoyl]-octahydrocyclopenta[b]pyrrole-2-carboxylic acid derivative of formula 2

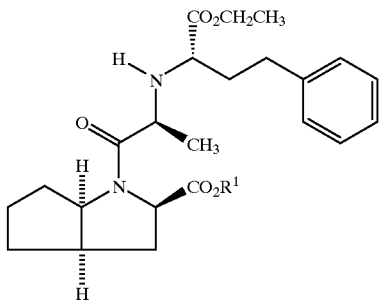

wherein $R^1$ H, the process comprising:
(a) treating the mixture of 1 and 2 with a solvent or mixture of solvents selected from a group consisting of $C_2$–$C_4$ nitrile solvents, $C_1$–$C_6$ alcohol solvents, $C_6$–$C_8$ aromatic hydrocarbon solvents, $C_3$–$C_{10}$ ether solvents, $C_3$–$C_6$ ketone solvents, $C_2$–$C_7$ ester solvents, $C_1$–$C_3$ halogenated solvents, and $C_5$–$C_{10}$ hydrocarbon solvents,
(b) adding an organic or inorganic base selected from a group consisting of sodium hydroxide, lithium hydroxide, potassium hydroxide, sodium bicarbonate, sodium carbonate, potassium carbonate, tert-butylamine, triethylamine, piperidine, aniline, n-butylamine or dicyclohexylamine, then filtering the slurry to obtain a solid salt of compound of formula 1.

30. The process of claim 29 where the solvent or mixture of solvents is selected from the group consisting of ethyl acetate, butyl acetate, ethyl propionate, isopropyl acetate, tert-butyl methyl ether, diisopropyl ether, toluene, dimethoxyethane, acetonitrile, ethanol and mixtures thereof.

31. The process of claim 29 where the solvent is ethyl acetate or a mixture containing ethyl acetate.

32. The process of claim 29 where the solvent is isopropyl acetate or a mixture containing isopropyl acetate.

33. The process of claim 29 where the solvent is acetonitrile or a mixture containing acetonitrile.

34. The process of claim 29 where the solvent is butyl acetate or a mixture containing butyl acetate.

35. The process of claim 29 where the salt produced is treated with an acid to give (2S,3aS,6aS)-1-[(S)-2-[[(S)-1-(ethoxycarbonyl)-3-phenylpropyl]amino]-propanoyl] octahydrocyclopenta[b]pyrrole-2-carboxylic acid (Ramipril).

36. The process of claim 1, 9, 20, or 29 wherein the precipitation temperature is –15 to 30° C.

* * * * *

UNITED STATES PATENT AND TRADEMARK OFFICE
CERTIFICATE OF CORRECTION

PATENT NO. : 6,407,262 B1
DATED : June 18, 2002
INVENTOR(S) : Zhi-Xian Wang and Cameron McPhail It is certified that error appears in the above-identified patent and that said Letters Patent is hereby corrected as shown below:

<u>Title page,</u>
Insert item:
-- [30]  Foreign Application Priority Data
Nov. 21, 2001 (CA)..........................2,363,658 --

Signed and Sealed this

Eighteenth Day of March, 2003

JAMES E. ROGAN
*Director of the United States Patent and Trademark Office*